United States Patent [19]
Michelson

[11] Patent Number: 6,083,228
[45] Date of Patent: Jul. 4, 2000

[54] DEVICE AND METHOD FOR PREPARING A SPACE BETWEEN ADJACENT VERTEBRAE TO RECEIVE AN INSERT

[76] Inventor: Gary K. Michelson, 438 Sherman Canal, Venice, Calif. 90291

[21] Appl. No.: 09/094,036

[22] Filed: Jun. 9, 1998

[51] Int. Cl.[7] .................................................. A61B 17/00
[52] U.S. Cl. ............................................................. 606/79
[58] Field of Search ........................... 606/79, 80, 81, 606/82, 85, 167, 168, 169, 170, 171, 180

[56] References Cited

U.S. PATENT DOCUMENTS

| | | | |
|---|---|---|---|
| 3,937,222 | 2/1976 | Banko | 606/80 |
| 4,842,578 | 6/1989 | Johnson et al. | 604/22 |
| 5,387,215 | 2/1995 | Fisher | 606/79 |
| 5,601,556 | 2/1997 | Pisharodi | 606/61 |
| 5,853,415 | 12/1998 | Bertin et al. | 606/80 |
| 5,904,687 | 5/1999 | Del Rio et al. | 606/80 |

*Primary Examiner*—Michael Buiz
*Assistant Examiner*—Tan-Uyen T. Ho
*Attorney, Agent, or Firm*—Martin & Ferraro, LLP

[57] ABSTRACT

A device and method for use in a human spine to prepare a space between adjacent vertebral bodies and into the vertebral end plates to receive an implantable insert. The device includes a handle, a shaft, and a mounting member at one end of the shaft. An abrading element is mounted on the mounting member and is coupled to a drive mechanism. The drive mechanism is operable to move the abrading element in at least one degree of freedom to create surfaces having predetermined contours in the end plates of the adjacent vertebral bodies.

162 Claims, 8 Drawing Sheets

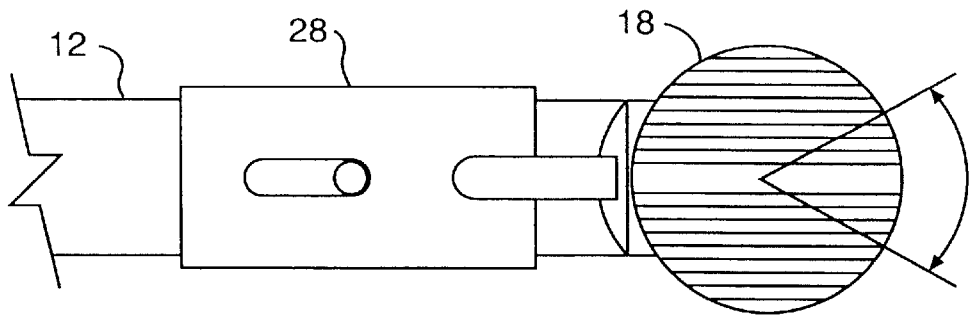
FIG. 4
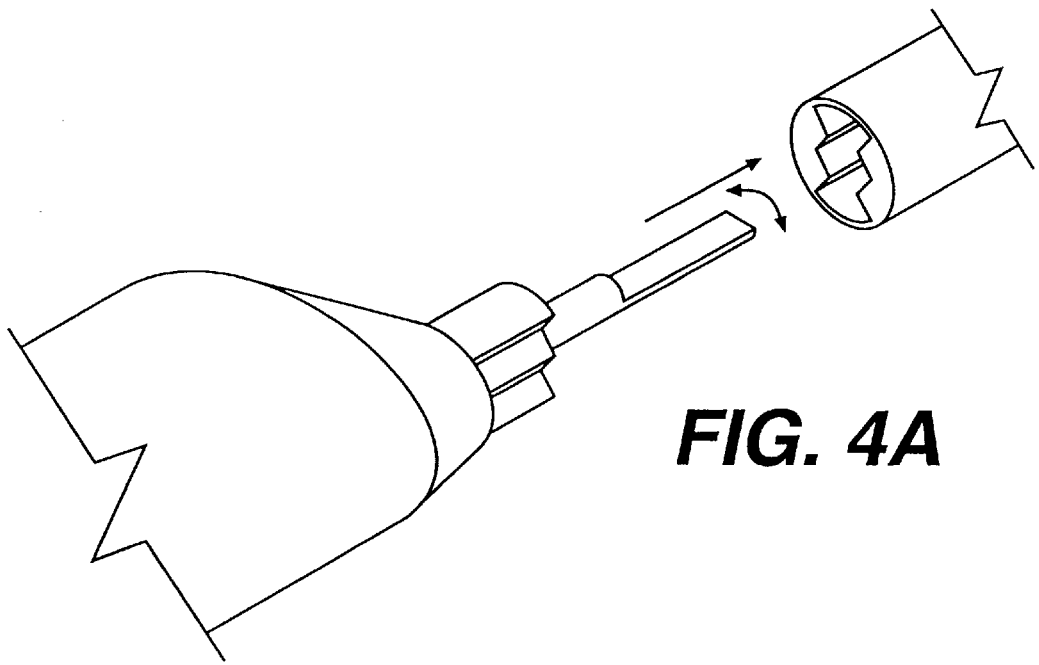
FIG. 4A
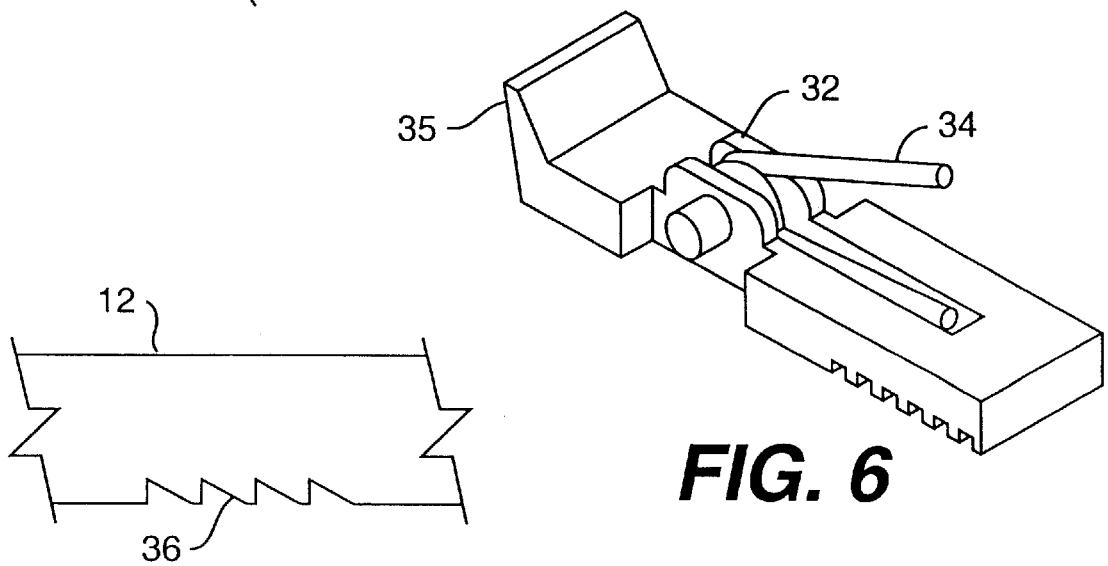
FIG. 5
FIG. 6

DEVICE AND METHOD FOR PREPARING A SPACE BETWEEN ADJACENT VERTEBRAE TO RECEIVE AN INSERT

FIELD OF THE INVENTION

The present invention relates to a device for insertion into a disc space between adjacent vertebral bodies in the human spine, and a method of working on those portions of the vertebral bodies adjacent that disc space to remove bone material and thereby access vascular bone. The device and associated method forms a surface on each of the vertebral body surfaces that are adjacent the intervertebral disc space, either sequentially, or in an alternative embodiment, simultaneously. The formed surface(s) have a shape and a contour corresponding to an interbody spinal insert to be implanted in the disc space.

BACKGROUND OF THE INVENTION

Inserts for placement between adjacent vertebrae in the spine come in a variety of shapes and sizes and are made of a variety of materials. Such inserts may or may not be designed to promote fusion of the adjacent vertebral bodies. Inserts not intended to participate in or to promote fusion of the adjacent vertebrae, for example an artificial spinal disc, are intended to maintain the spacing between the adjacent vertebrae and to permit relative motion between those vertebrae. Such inserts may or may not include some type of surface treatment or structure designed to cause the vertebrae to attach and grow onto the surface of the insert to thereby stabilize the insert. Another type of insert comprises bone grafts. Such bone grafts are typically intended to participate in and to promote fusion of the adjacent vertebrae. Another type of insert for use in human spinal surgery comprises implants made of selected inert materials, such as titanium, that have a structure designed to promote fusion of the adjacent vertebrae by allowing bone to grow through the insert to thereby fuse the adjacent vertebrae. This last type of insert is intended to remain indefinitely within the patient's spine.

The first known example of this last type of insert (for use in humans) is described in U.S. Pat. No. 5,015,247, which, in its preferred embodiment, discloses a hollow, threaded, cylindrical, perforated fusion implant device made of a material other than and stronger than bone and which is intended to cause fusion of adjacent vertebral bodies. A fusion promoting material, such as cancellous bone for example, is packed within the hollow portion of the implant and participates in the fusion. As used herein, the term fusion defines the growth of bone tissue from one vertebral body across a disc space to an adjacent vertebral body to thereby substantially eliminate relative motion between those vertebrae.

Human vertebral bodies are comprised of a hard outer shell of cortical bone (sometimes referred to as the cortex) and a relatively softer, inner mass of cancellous bone. Just below the cortical bone is a layer referred to as the subchondral plate. The outer shell of cortical bone that is adjacent the disc and the underlying subchondral plate are together herein referred to as the "end plate" and, for the purposes of this application, is hereby so defined to avoid ambiguity. The spinal disc that resides between adjacent vertebral bodies maintains the spacing between those vertebral bodies and, in a healthy spine, allows for relative motion between the vertebrae. At the time of surgery, for example in the instance where fusion is intended to occur between adjacent vertebral bodies of a patient's spine, the surgeon typically prepares an opening at the site of the intended fusion by removing some or all of the disc material that exists between the adjacent vertebral bodies to be fused. Because the outermost layers of bone of the vertebral end plate are relatively inert to new bone growth, the surgeon must work on the end plate to remove at least the outermost cell layers of bone to gain access to the blood-rich, vascular bone tissue within the vertebral body. In this manner, the vertebrae are prepared in a way that encourages new bone to grow onto or through an insert that is placed between the vertebrae.

Present methods of forming this space between adjacent vertebrae generally include the use of one or more of the following: hand held biting and grasping instruments known as rongeurs; drills and drill guides; rotating burrs driven by a motor; and osteotomes and chisels. Sometimes the vertebral end plate must be sacrificed as occurs when a drill is used to drill across the disc space and deeper into the vertebrae than the thickness of the end plate. Such a surgical procedure necessarily results in the loss of the hardest and strongest bone tissue of the vertebrae—the end plate—and thereby robs the vertebrae of that portion of its structure best suited to absorbing and supporting the loads placed on the spine by everyday activity. Nevertheless, the surgeon must use one of the above instruments to work upon the adjacent end plates of the adjacent vertebrae to access the vascular, cancellous bone that is capable of participating in the fusion and causing active bone growth, and also to attempt to obtain an appropriately shaped surface in the vertebral bodies to receive the insert. Because the end plates of the adjacent vertebrae are not flat, but rather have a compound curved shape, and because the inserts, whether made of donor bone or a suitable implant material, tend to have a geometric rather than a biologic shape, it is necessary to conform the vertebrae to the shape of the insert to be received therebetween.

It is important in forming the space between the adjacent bone structures to provide a surface contour that closely matches the contour of the inserts so as to provide an adequate support surface across which the load transfer between the adjacent bone structures can be evenly applied. In instances where the surgeon has not been able to form the appropriately shaped space for receiving the inserts, those inserts may slip or be forcefully ejected from the space between the adjacent vertebrae, or lacking broad contact between the insert and the vertebrae, a failure to obtain fusion may occur.

Furthermore, no known prior art device for preparing the vertebral end plates to receive an insert includes a working element that corresponds in shape, size, or contour to the shape of the insert to be implanted. That is, the known devices must be moved from side to side and in and out within the intervertebral space by an amount that exceeds the dimensions of the working element of the device, e.g., the rotating burr of a motor driven routing instrument or the working end of known osteotomes and chisels.

OBJECTS OF THE PRESENT INVENTION

It is an object of the present invention to provide a device and method for quickly, safely, effectively, and accurately working upon a vertebral body end plate adjacent a disc space so as to, while preserving that end plate at least in part, remove bone to produce a receiving surface corresponding in size, shape, and contour to an insert to be implanted between the adjacent vertebrae.

It is a further object of the present invention, in at least certain embodiments, to provide a device capable of simultaneously working upon both of the vertebral body end plates adjacent a disc space to produce opposed receiving surfaces in the adjacent end plates corresponding in size, shape and contour to an insert to be implanted, and in so doing to define the shape to the insert space.

It is a further object of the present invention to provide a vertebral interspace preparation device that, in a preferred embodiment, is capable of working with linear insertion, i.e., insertion along a single axis, and without the need to substantially move the device from side to side within the disc space along a second axis. In such a preferred embodiment, the device has at its working end an abrading element having a width generally corresponding to the width of the insert to be implanted.

It is a further object of the present invention to have a safety mechanism built into the device that limits the depth of insertion of the device into the spine.

It is a further object of the present invention to provide a vertebral interspace preparation device that has interchangeable ends so as to be capable of producing a variety of differently sized and contoured surfaces and shapes within the intervertebral space.

It is a further object of the present invention to have abrading surfaces extending to the leading end of the device such that the device may remove bone along its leading end as it is advanced within the disc space.

These and other objectives of the present invention will occur to those of ordinary skill in the art based on the description of the preferred embodiments of the present invention described below. However, not all embodiments of the inventive features of the present invention need achieve all the objectives identified above, and the invention in its broadest aspects is not limited to the preferred embodiments described herein.

BRIEF DESCRIPTION OF THE DRAWINGS

FIG. 4 is a second top view of the device shown in FIG. 1 and also illustrates the preferred range and type of motion of the abrading element;

FIG. 4A is a partial view of the device of FIGS. 1–4 showing a preferred mechanism for connecting the handle to the device shaft;

FIG. 5 is a detailed view of a portion of the device shaft illustrating notches used to hold a stop member in a selected position;

FIG. 6 is a detailed view of a spring-biased lever mechanism that may be used to adjust the position of a stop member;

SUMMARY OF THE INVENTION

Figure 1:
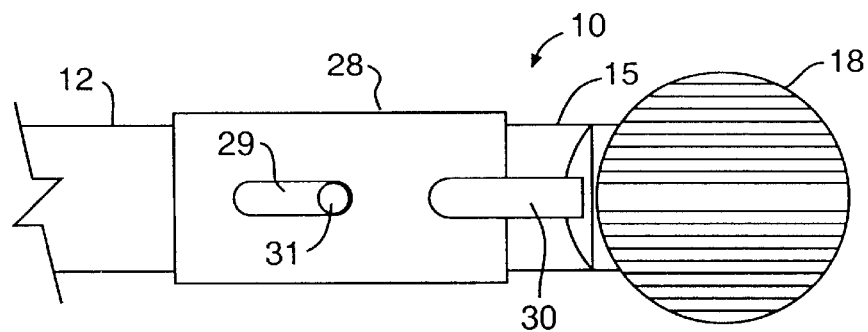
FIG. 1 is a partial top view of a first preferred embodiment of a device embodying the present invention, which device includes an abrading element having a single abrading surface.

The device, in its preferred embodiment, generally comprises an abrading element movably and replaceably mounted on the distal end of a shaft, and a depth limiting mechanism to control the depth of insertion of the abrading element into the intervertebral space (i.e., the disc space). The device also includes a handle that may be detachable from the shaft. As used herein, the term "handle" refers to a portion of the device that a surgeon may grip or otherwise manipulate to guide the working end of the device. That "handle" may, in fact, have multiple purposes. For example, the handle may be a portion of the shaft on which the abrading element is mounted at one end. Alternatively, the handle may be part of a segment that connects the device to a power source, for example, part of a conduit that supplies pressurized gas if the power source is turbine driven. In any event, the term "handle" is used herein in its broadest context to refer to that portion of the device that the surgeon chooses to grasp.

Additionally the shaft may be detachable from the abrading element. The device also includes a drive mechanism for transmitting power to activate, i.e., move, the abrading element, and the drive mechanism is connected to an energy source, e.g., a rechargeable battery, that may be housed within the handle of the device. By way of example only, the drive mechanism may comprise an electric motor or an electromagnetic oscillating mechanism. Or, again by way of example only, the drive mechanism and handle in which it is disposed may comprise the head unit of a gas powered turbine of the type commonly used in other surgical instruments.

In the preferred embodiment, the abrading element is generally as wide as the insert to be implanted between the adjacent vertebral bodies adjacent the disc space. The receiving bed, i.e., the prepared surface of the vertebrae, when formed by the device, will correspond in shape, size, and contour to the corresponding surfaces of the insert to be implanted. By way of example only, the surface produced may be flat or concave, or of some other desired shape and size so as to correspond to the upper or lower vertebrae contacting surfaces of the insert that will be implanted between the vertebrae. The device may also include a leading end that is capable of cutting through bone and/or disc material to form a pocket having a contour corresponding to the forward aspect and leading end of the insert to be implanted.

In a first preferred embodiment, the abrading element includes a single abrading surface that works on one vertebral surface at a time within the disc space.

In a second preferred embodiment, the abrading element includes a pair of opposed, outwardly facing abrading surfaces which lie in planes that may be either parallel to each other or, alternatively, convergent to each other. This embodiment of the present invention offers the further benefits of saving time by simultaneously preparing both of the vertebral end plates adjacent a disc space. The second embodiment not only includes the ability to simultaneously create two opposed surfaces, but also to shape the three-dimensional space that will be created between the adjacent vertebrae, which shape can be made to conform to the desired lordosis of that portion of the spine that will receive the insert.

However, the abrading element of the present invention is not limited to being a unitary, one piece construction, regardless of the number of abrading surfaces the abrading element may have. The abrading element may comprise multiple pieces that, by way of example and not limitation, are mountable on the end of the device to, in combination, define the overall shape of the abrading element and its abrading surface or surfaces. Thus, the term "abrading element" is used herein to refer to both a unitary, one piece construction or a multi-piece construction.

Thus, the present invention provides a device and method for preparing a disc space between adjacent vertebral bodies to receive an insert, and prepares that disc space by removing a portion of the end plate of the vertebrae adjacent that disc space to form predetermined surfaces in the end plates.

The prepared surfaces are sized and contoured to have broad intimate contact with the insert to be implanted between the adjacent vertebrae, which broad contact provides for increased implant stability. This broad area of intimate contact between the vertebrae and the insert promotes bone ingrowth from the vertebrae into the insert, and also provides a broad area over which to support the incumbent loads so as to minimize the risk of vertebral collapse or subsidence of the insert into the vertebra.

The abrading element is mounted on the mounting member and may be removable and interchangeable. In such an embodiment, the mounting member may be, but does not have to be, attachable to a shaft that is attachable to the handle. The abrading element and the mounting member may be separable from each other. Alternatively, the abrading element and the mounting member may, together, be removable from the handle. Various configurations of the abrading element and its abrading surface or surfaces can be used to form various contours in the adjacent vertebral bone structures.

In the instance where the abrading element has one abrading surface, the opposite surface of the abrading element, or the opposite surface of the mounting member, may be specifically designed to be non-abrading to the opposed adjacent vertebral end plate. Such a non-abrading surface may be designed to provide a mechanical advantage (such as achieved with a fulcrum) to allow the surgeon to increase the pressure of the abrading surface against the end plate being worked on, and, further, may be curved so as to be centering within the disc space by contact with a vertebral surface.

While the preferred embodiment of the present invention is discussed and disclosed herein with respect to creating a space between adjacent vertebrae in the spine, the present invention is not limited to a device for creating a space between adjacent vertebrae, but can also be used in other portions of the body where it is desirable to place an insert between adjacent bone structures. Furthermore, and as alluded to above, an embodiment of the present invention may have upper and lower abrading surfaces that are in angular relationship to each other so as to, for example, match the natural lordotic curvature of the human spine at the location of the vertebrae to be operated upon. Similarly, certain of the abrading surfaces of the abrading element may be configured with a convex, or even compound, geometry so as to form surfaces in the adjacent bone structures having a desired contour. Additionally, sequentially larger ones of the abrading element, or mounting member, may be used to form the desired space in a step-wise fashion, or the abrading element may be sized to substantially match the final desired width of the surface to be formed in the vertebral end plate. Furthermore and also as noted above, the abrading element may be configured with a sharpened leading edge to allow the abrading element to "forward cut" as it is inserted between the adjacent vertebrae. In this manner, progressive insertion of the abrading element between the vertebrae can be facilitated.

While the present invention has been generally described above, and the preferred embodiments of that invention will be described in detail below, neither that general description nor the detailed description limits the scope of the present invention. That scope is defined solely by the claims appearing at the end of this patent specification.

DETAILED DESCRIPTION OF THE PRESENTLY CONTEMPLATED EMBODIMENTS

Figure 1A:
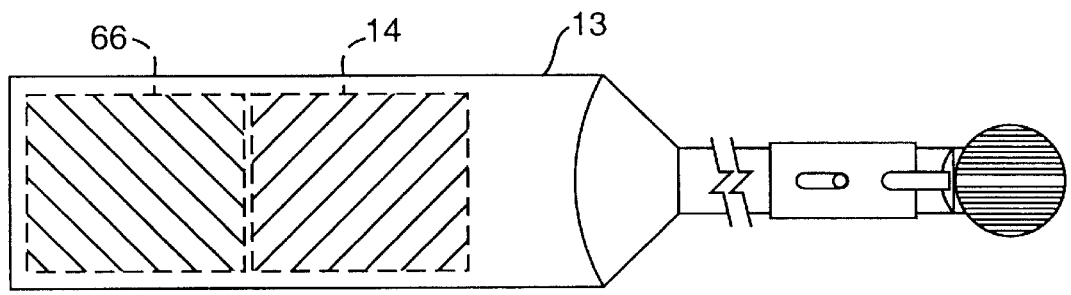
FIG. 1A is a full top view of the device of FIG. 1 illustrating the handle of the device.

With reference to FIGS. 1 and 1A, a first embodiment of the present invention comprises a disc space preparation device generally referred to by numeral 10. Device 10 includes a shaft 12 and a handle 13. Handle 13 may be formed with any number of known shapes designed to make the surgeon's grip on the handle more secure or comfortable. Similarly, handle 13 may include a soft rubber covering or may be formed, at least partially, of a material designed to promote a secure grip of the surgeon's hand on the handle. Those of ordinary skill in the art will recognize the many types of surface configurations or materials of which the handle can be made to achieve these goals.

Figure 2:
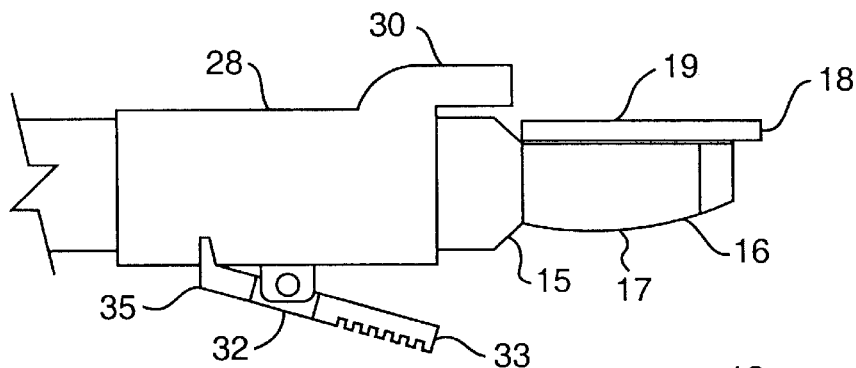
FIG. 2 is a side view of the device shown in FIG. 1.

With continued reference to FIGS. 1 and 1A, disposed within handle 13 is a drive mechanism diagrammatically depicted by box 14. Although in the embodiment of the device shown in FIGS. 1 and 1A the drive mechanism 14 is disposed within handle 13, it need not be disposed in the handle. The drive mechanism may be disposed completely or partially outside of the handle, for example, where the drive mechanism is a gas powered turbine element such as is used in some known surgical instruments. Drive mechanism 14 is operably connected to the proximal end of shaft 12 and is capable of moving an abrading element 18 disposed at a distal end 15 of shaft 12. Abrading element 18 has an abrading surface 19. Drive mechanism 14 moves abrading element 18 at a sufficiently high rate to quickly and efficiently cause abrading surface 19 to form the desired space and the desired surface contours in the adjacent vertebral bone structures. As illustrated in FIG. 2, the abrading element 18 is mounted on a mounting member 16 disposed at the distal end 15 of shaft 12. In this embodiment, the mounting member is fixed to shaft 12 and only the abrading element moves. However, many alternative mechanisms for mounting the abrading element on the device are possible within the scope of the present invention, including a mechanism wherein mounting member 16 is movably attached to shaft 12 and the drive mechanism moves both the mounting member and the abrading element attached thereto. Also, mounting member 16 may be designed with a surface 17 on the side of the mounting member 16 opposite abrading element 18. Surface 17 is designed, in the embodiment shown, to bear against the end plate that is opposite the end plate being worked on by abrading element 18. In this manner, surface 17 provides a bearing surface that the surgeon may use to gain a mechanical advantage (such as with a lever) to contact abrading surface 19 of abrading element 18 against the end plate being worked on. Additionally, surface 17 may be curved as shown in FIG. 2, or otherwise shaped, to contact one end plate and, thereby, center or otherwise position abrading element 18 in the disc space.

As presently contemplated, the motion of the abrading element may be vibratory, reciprocatory, oscillatory, or rotary. In the first preferred embodiment of device 10, the motion of the abrading element is rotary in a clockwise then counterclockwise direction through a preferred range of motion of between 20° to 45°, as illustrated in FIG. 4. Whatever type and range of motion is selected for the abrading element, it will likely, although not necessarily, be in a direction that is generally parallel to the plane of the surface to be formed in the vertebral end plate. However, since the shape of that surface contour is not necessarily flat, neither is the direction of the motion of the abrading element necessarily parallel to all points on that desired surface contour.

By way of example and not limitation, the drive mechanism may comprise a magnetic driver of the type described in U.S. Pat. No. 5,263,218. Alternatively, the drive mechanism may take the form of a mechanical drive utilizing a cam mechanism such as described in U.S. Pat. No. 5,383,242. Additionally, drive mechanisms used in known surgical power milling apparatus may also be used. As presently contemplated, the drive mechanism should be capable of moving the abrading element and its abrading surface or surfaces at a speed sufficient to abrade the hard cortical bone of the vertebral end plate. The working range and speed of motion of the drive mechanism will be readily selected by those of skill in the art.

In one embodiment of the present invention utilizing reciprocating motion, the stroke or amount of reciprocating movement is relatively small and can be selected as desired to achieve the purpose of abrading the adjacent bone structures. That stroke may be selected based on the relative strength of the bone structures to be abraded, the relative strength of the material forming the abrading element, and the type of surface roughening formed on one or more surfaces of the abrading element. This relatively small reciprocating movement of the abrading element results in a tightly controlled excursion area between the adjacent vertebrae being prepared to receive an insert. In contrast, a motorized burr must be moved free hand and in a side-to-side motion within the disc space by the surgeon to form a space to receive an insert. Thus, use of such a motorized burr does not provide a way of forming a precise surface shape in the vertebral end plate. Additionally, because the motorized burr rotates in a single direction, it may catch on a piece of the vertebra and cause the burr to jerk forcefully out of the intervertebral space. Such an occurrence will not happen with the device 10 because of the controlled excursion of the device.

In the first embodiment of the present invention described herein, drive mechanism 14 is powered by a rechargeable battery illustrated as box 66 in FIG. 1A. Battery 66 is also preferably located within handle 13 of device 10. However, the present invention is not limited to use with a rechargeable and/or replaceable battery 66, but may also be configured to run on any standard electrical source, such as 110 volt, 60 cycle power sources, with or without the accompanying use of a transformer to reduce that voltage as may be necessary and desirable. Alternatively, the drive mechanism may comprise a gas turbine mechanism as is common for many types of powered surgical instruments. The particular power source that powers drive mechanism 14 does not form a part of the present invention except to the extent it is adapted to achieve the appropriate and desirable amount of movement of the abrading element.

Referring now to FIG. 2, which shows a portion of device 10 in side view, mounting member 16 extends from the distal end 15 of shaft 12. As described below with reference to FIGS. 7–10, the mounting member may be configured to house a portion of a coupling mechanism that, in turn, couples drive mechanism 14 to an abrading element 18 to move the abrading element in at least one degree of freedom while the mounting member remains stationary relative to the handle. The term "degree of freedom" is used herein in its ordinary sense to refer to motion in a standard three-dimensional environment. That three dimensional environment may be defined by X, Y, and Z axes. In such a three-dimensional environment, 6 degrees of freedom exist: translational motion along each of the X, Y, and Z axes, and rotational motion about each of the X, Y, and Z axes. Thus, drive mechanism 14 is operable to move abrading element 18 in a reciprocating, oscillating, or vibrating motion transversely along one or more of the X, Y, and Z axes. Alternatively, or in conjunction, drive mechanism 14 may be configured to move abrading element 18 around one or more of the X, Y, or Z axes. Of course, for purposes of achieving the objectives of the present invention, it may not be necessary that the drive mechanism reciprocate or oscillate mounting member 16 in anything more than a single degree of freedom.

Figure 7:
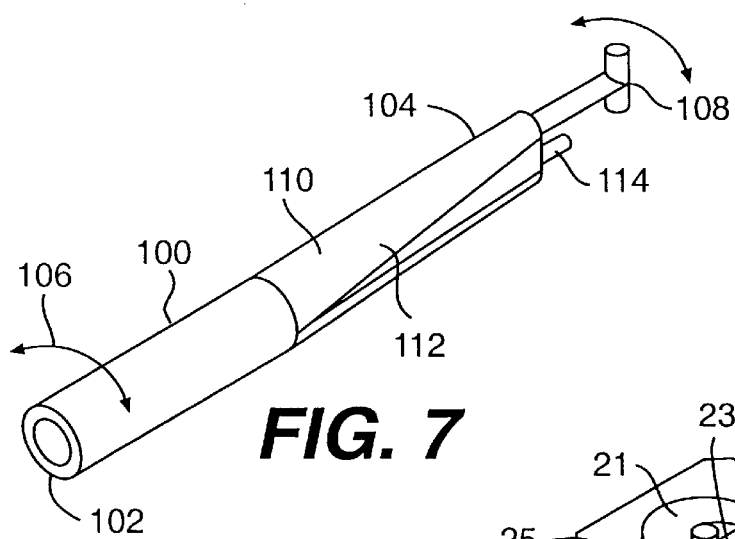
FIG. 7 is a detailed view of a coupling mechanism that may be used to movably couple the drive mechanism to the abrading element.
Figure 8:
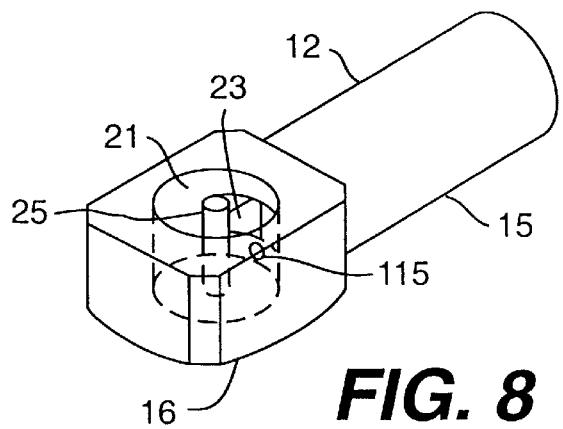
FIG. 8 is a detailed view of the mounting member disposed at the distal end of the device shaft.
Figure 9:
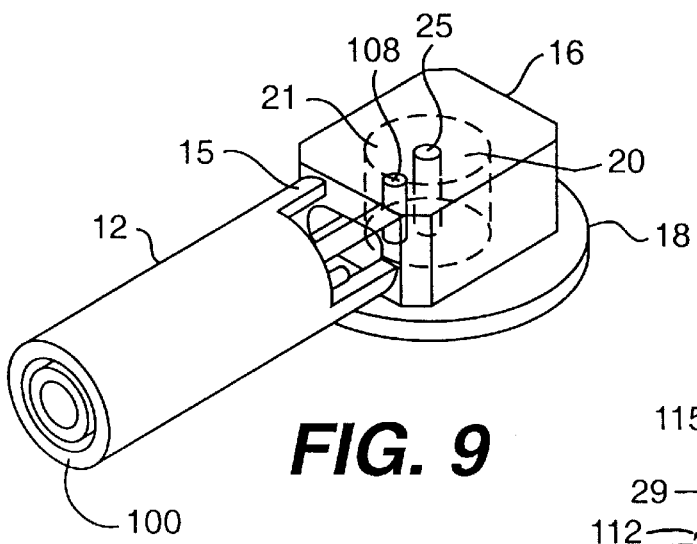
FIG. 9 is a further detailed view of the coupling mechanism and mounting member illustrated in FIGS. 7 and 8.
Figure 10:
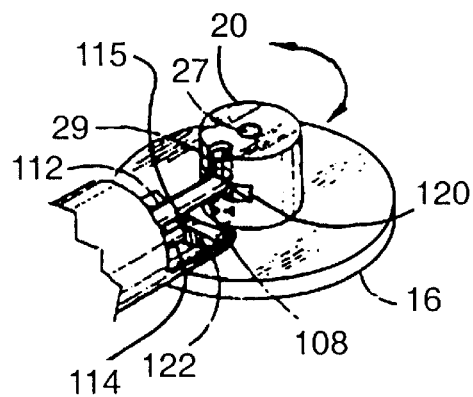
FIG. 10 is a detailed view illustrating a preferred way of movably connecting the coupling mechanism to the abrading element.

Referring now to FIGS. 7–10, in a present preferred embodiment, abrading element 18 includes a projection 20 (as best seen in FIG. 10) that is to be received in a corresponding aperture 21 formed in mounting member 16 (as best seen in FIG. 8). Mounting member 16 may be fixedly disposed on distal end 15 of shaft 12. Alternatively, mounting member 16 may be removably attached to distal end 15 of shaft 12. In the present embodiment, a coupling mechanism is used to couple abrading element 18 to mounting member 16 and to the drive mechanism. FIG. 10 illustrates that coupling mechanism with mounting member 16 removed to show in clearer detail the coupling mechanism.

With reference to FIGS. 7 and 9, the coupling mechanism in the first preferred embodiment of the present invention comprises a generally tubular member 100 received within a hollow, longitudinal aperture of shaft 12. Tubular member 100 includes a proximal end 102 and a distal end 104. A T-shaped connector 108 is configured at the end of a drive rod 112. Drive rod 112 is adapted to be received within a corresponding aperture 110 in tubular member 100. A pivot rod 114 extends from the distal end 104 of tubular member 100 and is adapted to fit in a corresponding hole 115 formed in mounting member 16 at the end of shaft 12.

With reference to FIG. 8, mounting member 16 includes a central aperture 21 and an oblong slot 23 formed through a wall of mounting member 16. Slot 23 is configured to allow connector 108 to pass through when the connector is turned (as illustrated by the arrows in FIG. 7) so that the branches forming the "T" extend laterally. Mounting member 16 also includes a post 25 that projects into aperture 21. Post 25 is sized to mate with an aperture 27 formed in projection 20 of abrading element 18 as shown in FIG. 10. Projection 20 is also formed with a slot 29 designed to receive connector 108 as described below.

With reference to FIG. 9, tubular member 100 fits within shaft 12 with connector 108 extending from distal end 13 of the handle. Projection 20 of abrading element 18 is inserted into aperture 21 of mounting member 16 such that post 25 fits into aperture 27 of projection 20. Connector 108 is initially rotated such that its "T" branch fits through slot 23 of mounting member 16 and then is rotated 90° as shown by the arrows in FIG. 7. With the "T" branches of connector 108 extending parallel to post 25, projection 20 of abrading element 18 fits into aperture 21 of mounting member 16 such that connector 108 fits into slot 29, and post 25 fits into aperture 27.

FIG. 10 shows the same structure as FIG. 9 but with mounting member 16 removed for purposes of better illustrating the mating of connector 108 with slot 29. As shown in FIG. 10, pivot rod 114 fits into a mating aperture 115 formed at the distal end of shaft 12, and projection 20 includes a second slot 120 formed laterally from slot 29. Slot 120 is configured to allow connector 108 to toggle back and forth as tubular member 100 is reciprocatingly pivoted about pivot rod 114 by the device's drive mechanism. This "toggling" action of member 100 about pivot rod 114 moves T-shaped connector 108 and abrading element 18 in the direction indicated by the double headed arrow in FIG. 10.

Of course, many variations exist for mechanisms to couple the drive mechanism 14 to abrading element 18. The coupling mechanism described above is provided by way of example and not limitation.

In the embodiment described, mounting element 16 may interchangeably receive various ones of abrading element 18. Thus, abrading element 18 may be quickly and easily attached to and detached from mounting member 16 during surgery. While in the preferred embodiment the abrading surface of the abrading element is selected to have a width that is substantially the same as the width of the surface to be formed in the vertebral end plate (to eliminate any need to move the abrading element side to side in the disc space as noted earlier), a surgeon might also elect to use an abrading element that is smaller in width than the ultimate desired width of the surface to be formed. Thereafter, the surgeon may use successively larger abrading elements 18 until she arrives at the desired dimensions of the space formed between the adjacent bone structures. This approach also eliminates any need to significantly move the abrading element in a side to side path within the disc space.

Referring back to FIGS. 1 and 1A, device 10 includes at least one stop member 28 adjustably disposed on mounting element 16 to limit the travel of the abrading element into the adjacent bone structures. Stop member 28 includes an abutment 30 that will eventually contact the vertebrae to limit travel of the abrading element 18 as the abrading element forms the space between the adjacent vertebrae. Stop member 28 is not limited to a single abutment. Two or even more abutments may be formed around the circumference of stop member 28 and the leading edges of such multiple abutments may be configured to terminate at different positions relative to shaft 12. Other mechanisms for limiting the depth of insertion of the device into the disc space are possible, and this example is provided by way of illustration.

Figure 3:
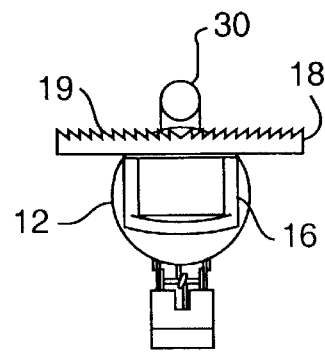
FIG. 3 is an end view of the device shown in FIGS. 1 and 2.

In the embodiment of stop member 28 shown in FIGS. 1, 2, and 3, a slot 29 is formed in stop member 28 and an extension 31 projects from shaft 12 through slot 29. Slot 29 is dimensioned to correspond to the desired maximum amount of adjustment of the stop member relative to the handle. As shown in FIG. 2, and in FIGS. 5 and 6, stop member 28 is held at a desired position on shaft 12 by spring-biased lever 32. Lever 32 includes an actuator end 33 with grooves, notches, knurls, or other surface preparation that is pushed toward shaft 12 against the bias of spring member 34 to lift engaging end 35 of lever 32 away from shaft 12. Engaging end 35 is configured to mate with notches 36 formed in shaft 12 as shown in FIG. 5. Notches 36 in shaft 12 are not visible in FIG. 2 since they are covered by stop member 28. Step member 28 is also formed with an opening sized to allow engaging end 35 of lever 32 to fit in notches 36. Numerous other structures for holding stop member 28 at a desired position on shaft 12 are possible, and spring biased lever 32 is provided in this embodiment of the present invention by way of example and not limitation. For instance, shaft 12 may include threads on a portion of its outer surface to receive a threaded adjusting collar that will lock stop member 28 in a desired position.

Figure 21:
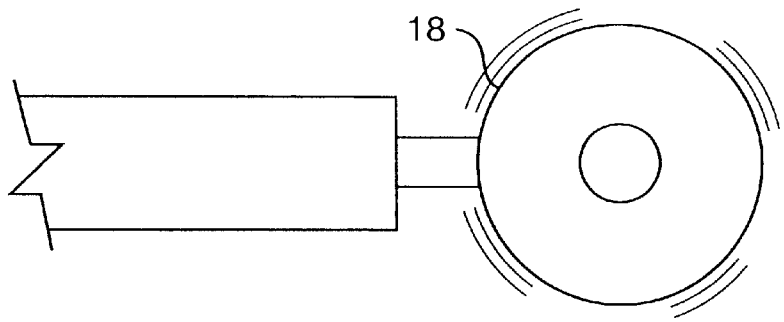
FIG. 21 illustrates an alternative path of motion possible for an abrading element according to the present invention.
Figure 22:
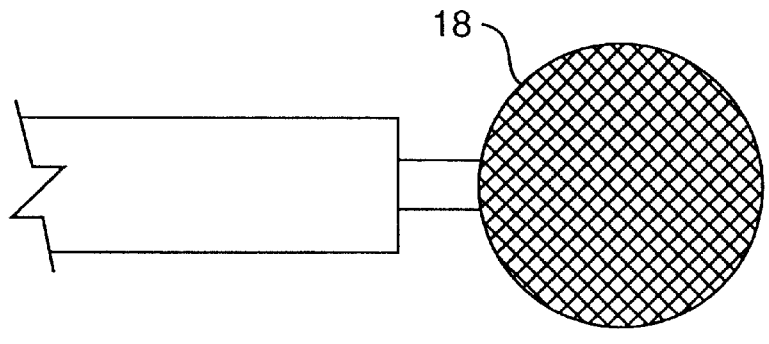
FIG. 22 illustrates a further alternative path of motion possible for the abrading element.

With reference to FIGS. 21 and 22, examples of the types of motion through which abrading element 18 may be moved are illustrated. In FIG. 21, the motion is vibratory in a plane generally parallel to the abrading surface of the abrading element. In FIG. 22, the motion is linear and reciprocating as indicated by the double headed arrow of that figure. Alternatively, the motion may comprise slight rotation about a pivot point near distal end 15 of shaft 12 such that the oscillation is arcuate about an axis extending into and out of the sheet of paper on which FIGS. 21 and 22 are illustrated. Other motions such as full and complete rotation as described below with reference to the second preferred embodiment are also useful.

Any of these types of motion will be adequate to cause the abrading surface or surfaces of abrading element 18 to abrade adjacent bone structures to thereby form the appropriately sized and dimensioned space between those bone structures for receiving an insert. In this regard, at least one or more of the surfaces of abrading element 18 is roughened such that it can abrade the adjacent bone structures.

Figure 11:
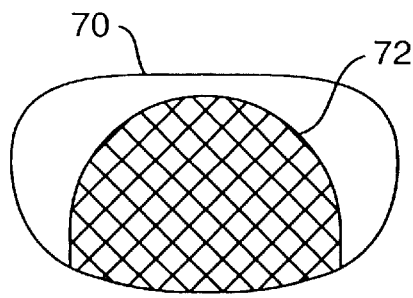
FIG. 11 is top view of a first vertebral body having a surface prepared in one of the end plates by a device incorporating the present invention.
Figure 12:
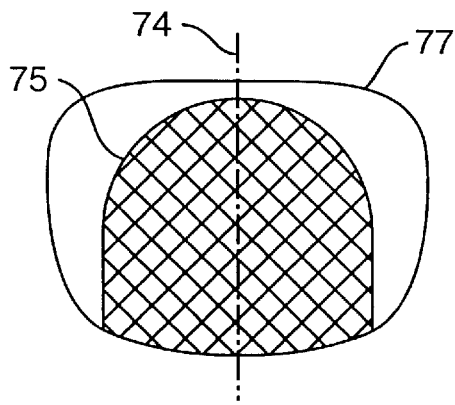
FIG. 12 is a top view of a second vertebral body, different than that shown in FIG. 11, having a surface prepared in one of the end plates by a device incorporating the present invention.
Figure 14:
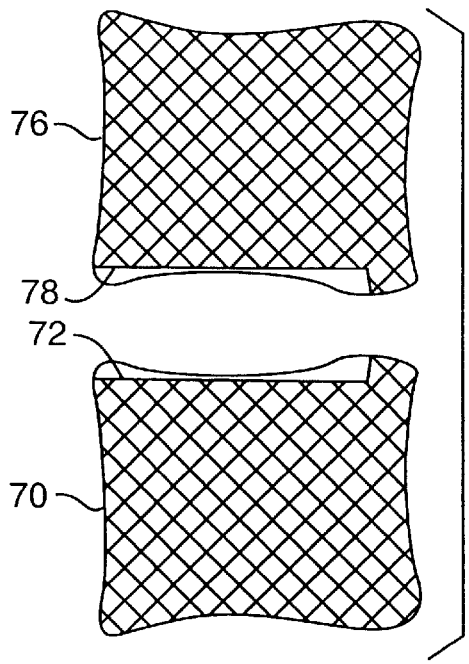
FIG. 14 is a cutaway side view of adjacent vertebral bodies having their respective adjacent end plates prepared by a device incorporating the present invention to form a space configured to receive an insert.
Figure 13:
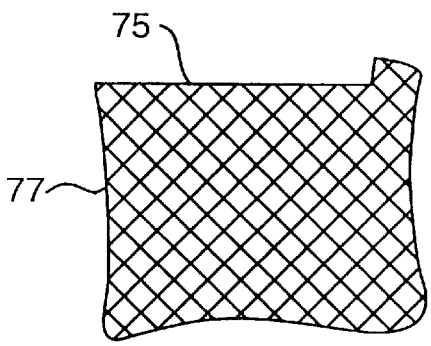
FIG. 13 is a cutaway side view of the vertebral body shown in FIG. 12.

FIGS. 11, 12, 13, 14, and 15 illustrate various views of vertebral bodies that have been worked on by a device incorporating the present invention. The cross-hatching in these figures represents the softer, blood rich cancellous bone of the vertebrae beneath the harder, outer cortical bone shell. FIG. 11 shows a top view of a first vertebral body 70 with a surface 72 formed by a circular abrading element 18 as shown in FIG. 1. The width of surface 72 formed on first vertebral body 72 closely matches the width of an abrading element 18 that was advanced into the disc space along a single front to back axis. A second vertebral body 77 has a greater depth than vertebral body 70. The second vertebral body 77 shown in FIG. 12 has a surface 75 formed by extending abrading element 18 deeper into the distal interspace along front-to-back axis 74. FIG. 13 illustrates a cutaway side view of the vertebral body shown in top view in FIG. 12. FIG. 14 shows a cutaway side view of adjacent vertebral bodies 70 and 76 that have had surfaces 72 and 78 formed in their respective adjacent end plates. Note that, as shown in exaggerated view in FIG. 15, the vertebral end plate surface is prepared to a uniform shape, which while preserving the deeper portions of the end plate, also forms a socket depressed from the hard cortical uprisings of bone such as the uncovertebral joints 80. Recognize that the depth of this remaining end plate is exaggerated in FIG. 15 to illustrate this result of using the present invention. This remaining portion of the more cortical rim 80 assists in retaining the insert in the desired position between the adjacent vertebrae by acting as an abutment preventing lateral or posteriad movement of the insert. The prepared faces of these abutment portions of the vertebral end plate also increase the surface area of contact between the insert and the vertebral body.

Figure 15:
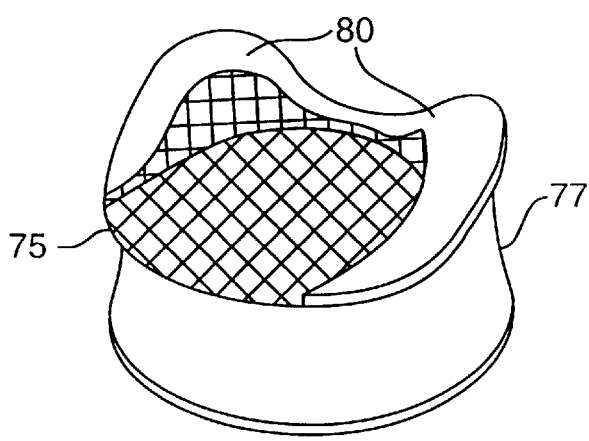
FIG. 15 is an exaggerated perspective view of the vertebral body illustrated in FIG. 12 showing the formation of the receiving surface in the vertebral end plate.
Figure 15A:
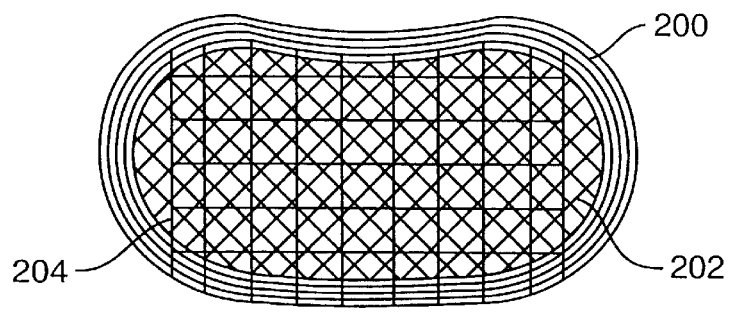
FIG. 15A is a top view of a section of a human spine illustrating the portion of the disc that is typically removed to accommodate the implantation of an intervertebral insert.

FIG. 15A illustrates, in top view, the ideal portion of a disc that is removed to accommodate implantation of the insert. In FIG. 15A, the annulus fibrosus is illustrated with rings 200 extending around the periphery of the intervertebral disc space. Inside the annulus fibrosus is the nucleus pulposus 202 illustrated in cross-hatching. The general area and volume of the nucleus pulposus to be removed with the device of the present invention is illustrated with additional cross-hatchings 204. The preferred dimensions of the space created by the device is generally not as wide as the entire nucleus pulposus.

Figure 16:
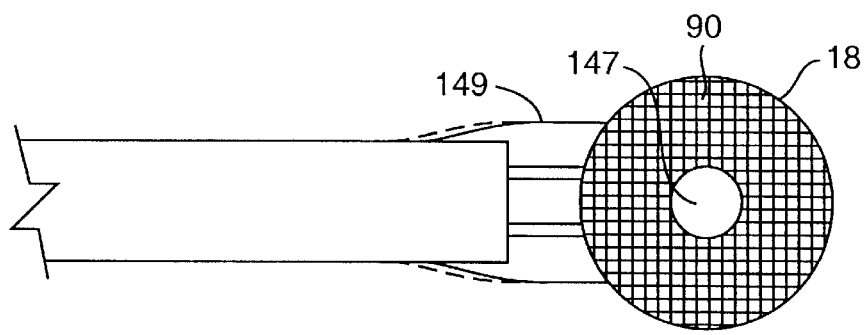
FIG. 16 is a top view of a second preferred embodiment of a device embodying the present invention, which device includes an abrading element having two abrading surfaces.
Figure 17:
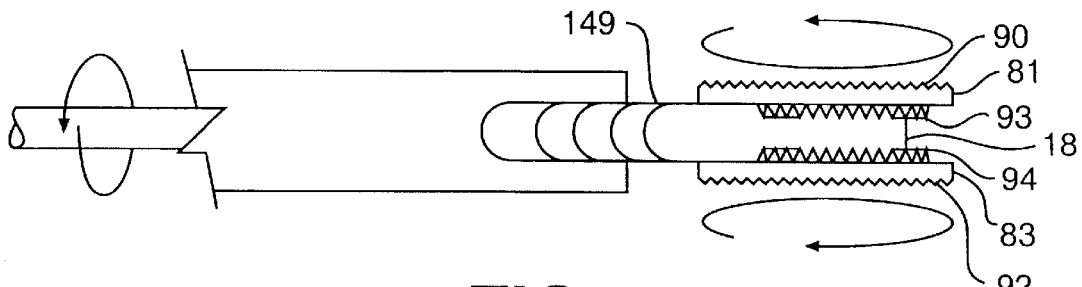
FIG. 17 is a side view of the device shown in FIG. 16.
Figure 17A:
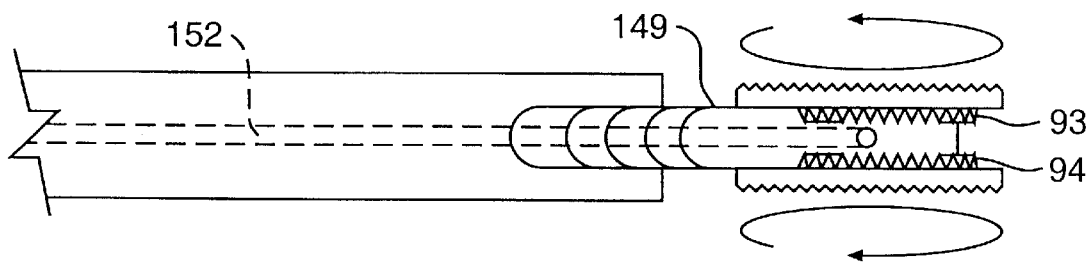
FIG. 17A is a side view of the device shown in FIG. 17.
Figure 17B:
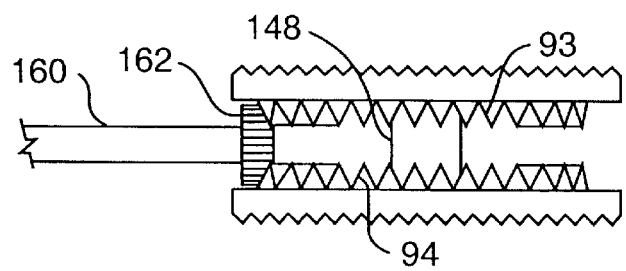
FIG. 17B is a detailed view of one possible drive mechanism that may be used with the second embodiment of the present invention.

Referring now to FIGS. 16 and 17, a second embodiment of the present invention is shown wherein abrading element 18 includes two abrading surfaces: an upper abrading surface 90 and a lower abrading surface 92. FIG. 16 is a top view of such a device and FIG. 17 is a side view. In this embodiment, abrading element 18 includes two disc shaped members, 81 and 83, that are mounted on the distal and of the device by a recessed screw 147 and screw shaft 148 as described below. Abrading surface 90 is formed on one side of disc-shaped member 81, and abrading surface 92 is formed on one side of disc-shaped member 83. Thus, the abrading element 18 illustrated in FIGS. 16 and 17 provides an example of an instance where the abrading element comprises multiple pieces that fit together to form the abrading element. As previously described, the present invention contemplates unitary, one piece constructions for the abrading element as well as multi-piece constructions. In the embodiment of the present invention shown in FIGS. 16 and 17, the upper and lower disc-shaped members 81 and 83 and their associated abrading surfaces may be rotated in opposite directions so as to counteract and balance any torque applied to the shaft and handle of the device as the abrading element digs into and abrades the vertebral end plates. This counter-rotation of the members 81 and 83 also prevents the device from being pulled to one side as the vertebral end plates are being worked on. This counter-rotating motion of the two members 81 and 83 is illustrated by the arrows in FIG. 17 and may be achieved, as illustrated in FIG. 17B, by using a spinning drive rod 160 that extends through shaft 12 and is configured with a gear 162 at its distal end that engages with mating gear teeth 93 and 94 formed on respective ones of disc-shaped members 81 and 83 as shown in FIGS. 17A and 17B. Disc shaped members 81 and 83 may be attached to the end of shaft 12 by a recessed screw 147 that is received in a mating, threaded screw shaft 148 as shown in FIG. 17B. Thus, in this second embodiment, the mounting member comprises threaded screw shaft 148 and recessed screw 147 disposed at the distal end of a tapered extension 149 that protrudes from shaft 12.

Figure 16A:
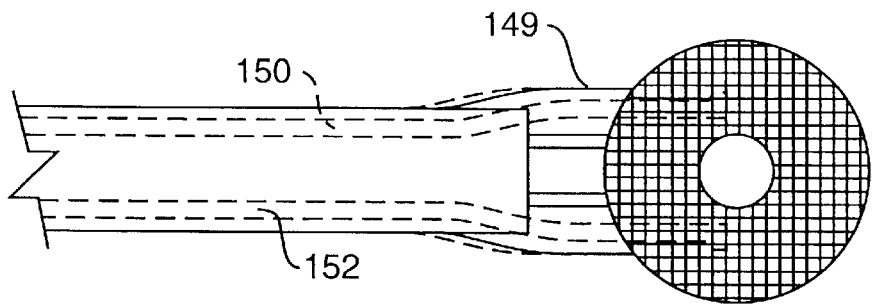
FIG. 16A is a top view of the device of FIG. 16 illustrating irrigation and suction tubes that may be incorporated into the device.

FIGS. 16A and 17A show a further enhancement to the device shown in FIGS. 16 and 17 wherein the shaft 12 also includes an irrigation tube 150 and a suction tube 152 that may be formed within, or outside of, shaft 12. These irrigation and suction tubes may be connected to appropriate sources of irrigation fluid and a source of vacuum, respectively, to efficiently irrigate and clear the surgical site during use of the device.

Figure 20:
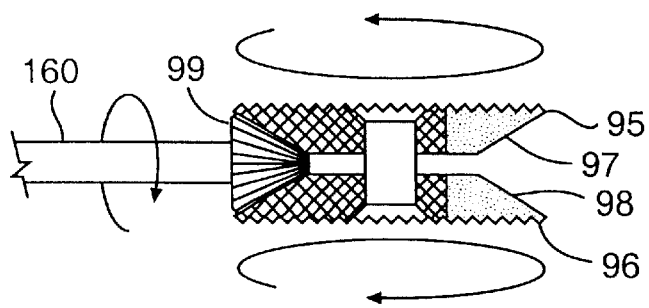
FIG. 20 shows an alternative embodiment of a mechanism for driving an abrading element.

Alternatively, and as shown in FIG. 20, upper and lower disc-shaped members 94 and 96 may be formed with inwardly sloping, ramped surfaces 97 and 98 that engage a cone-shaped driver 99 disposed on the distal end of a rotating drive rod 160 to turn the upper and lower abrading surfaces in opposite directions as the drive rod spins about its axis. Alternatively, the lower surfaces of the abrading element 18 and the cone-shaped driver can be radially splined to engage one another. Such a dual surface abrading element can simultaneously work on both adjacent end plates of adjacent vertebrae. Abrading member 18 having such dual abrading surfaces can even be constructed such that the distance between the abrading surface is adjustable to accommodate variations in the height of the disc space. By way of example and not limitation, paired, wedge-shaped blocks may be disposed between the abrading surfaces and an adjusting screw can be provided to extend through threaded apertures in each wedge-shaped block. As the adjusting screw is turned, the wedge-shaped blocks move relative to one another to change the distance between the abrading surfaces.

Figure 18:
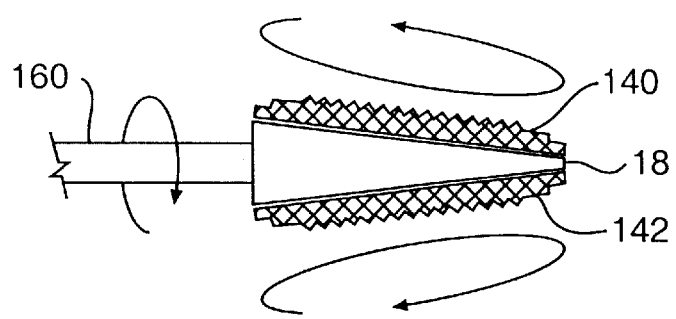
FIG. 18 is an alternative embodiment of an abrading element having two abrading surfaces, which abrading surfaces are inclined relative to one another to form a space between the adjacent vertebral bodies that approximates the lordotic curvature of a human spine at the location that will receive the interbody insert.

In a still further embodiment of the present invention as illustrated in FIG. 18, the abrading element 18 may have upper and lower abrading surfaces 140 and 142 that are angled or tilted relative to each other. The degree of angle or tilt may be selected to match the natural lordotic curvature of the spine at the location of the vertebrae to be worked on. The distance between the upper and lower abrading surfaces 140 and 142 in this embodiment may also be adjustable to accommodate differing disc heights between the vertebrae. Such angled abrading surfaces may also be driven in counter rotation by drive rod 160 as shown by the arrows in FIG. 18.

Figure 19:
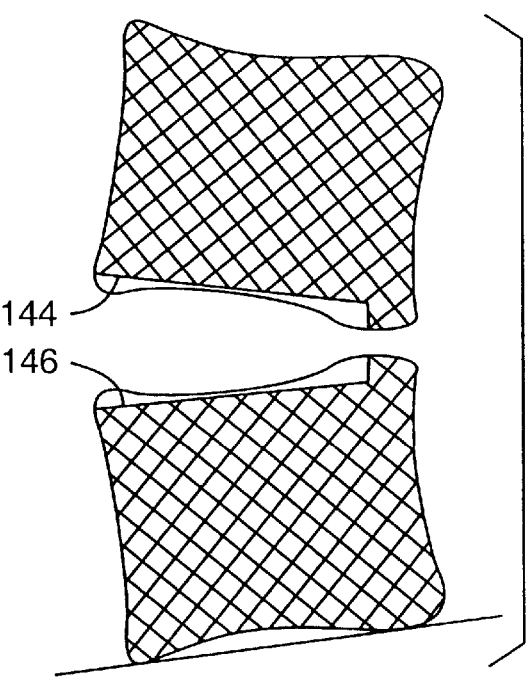
FIG. 19 is a cutaway side view of adjacent vertebral bodies showing a lordotically configured space created between the vertebrae by the abrading element shown in FIG. 18.

As illustrated in FIG. 19, the slope of the surfaces 144 and 146 formed in the adjacent vertebrae by the abrading element shown in FIG. 18 matches the lordotic curvature of the spine at that location.

Figure 23:
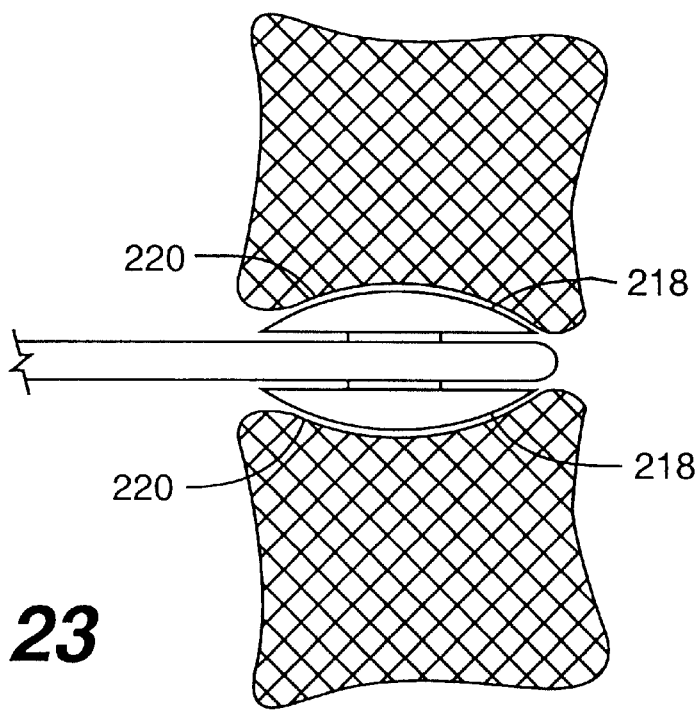
FIG. 23 illustrates an alternative configuration of the abrading element suitable for creating concave insert receiving surfaces on the adjacent vertebral end plates.

Numerous other configurations of abrading element 18 are possible within the scope of the present invention. For example and with reference to FIG. 23, abrading elements 218 may be convex to form concave receiving surfaces 220 in the vertebral end plates. The geometry and configuration of the shapes of the abrading elements can be matched to the desired shape and configuration of the space which the surgeon intends to create between adjacent bone structures and to the desired contour of the surfaces created in the bone structures.

Additionally, the abrading surface of abrading element 18 may be configured as roughenings, knurls, ridges, small pyramid shaped projections, or any other surface configuration that is capable of abrading the bone structures.

Where only one surface of the abrading element is configured to abrade an end plate of the vertebral body, an opposite surface (or the opposite surface of mounting member 16 as illustrated by element 17 in FIG. 2) may be configured to be supported by the adjacent end plate without causing any significant abrasion of that adjacent end plate. In such an instance, the non-abrading surface of the abrading element, or surface 17 of mounting member 16, may be configured to allow the surgeon to achieve a mechanical advantage that increases the bearing pressure of the abrading surface against the end plate being worked on, and also to locate and center the device. In this manner, one adjacent end plate provides mechanical support to the device while the device works on the adjacent end plate. After an appropriate surface is formed on one end plate, the device can be turned 180° to use the abrading surface on the other end plate.

Since any device incorporating the subject matter of the present invention is designed to be used within a surgical theater, it is desirable that the device be susceptible of sterilization by any one of many known expedients. In this regard, handle 12 of device 10 may be waterproof such that the device can be sterilized.

Although various embodiments of the present invention have been disclosed for purposes of illustration, it will be understood by those of ordinary skill in the art that changes, modifications, and substitutions may be incorporated in these embodiments without departing from the spirit or scope of the present invention as defined by the claims, which follow.

I claim:

1. A device for preparing a space in the human spine to receive an insert between adjacent vertebral bodies, comprising:
    a handle;
    a shaft operably connected to said handle;
    a mounting member disposed at a distal end of said shaft;
    a drive mechanism;
    a power source operably connected to said drive mechanism; and
    an abrading element mountable on said mounting member and movable by said drive mechanism, said abrading element having at least one abrading surface selected to create a predetermined surface contour in one of the adjacent vertebral bodies as the abrading element is moved by the drive mechanism.

2. The device of claim 1, wherein said mounting member is fixedly connected to said shaft.

3. The device of claim 1, wherein said mounting member is removably connected to said shaft.

4. The device of claim 1, wherein said mounting member includes an aperture and said abrading element includes a projection configured to fit within said aperture of said mounting member.

5. The device of claim 1, wherein said abrading surface is configured such that it is operated in a plane generally parallel to said surface contour formed in the vertebral body as the abrading element is moved by the drive mechanism.

6. The device of claim 1, wherein said mounting member includes a wall, an aperture, and a slot configured through said wall to communicate with said aperture.

7. The device of claim 1 including a mechanism that couples the abrading element to said drive mechanism.

8. The device of claim 7, wherein said coupling mechanism includes a drive rod having a proximal end and a distal end, said drive rod being adapted to be received in said shaft, said distal end of said drive rod being configured to couple to said abrading element to move said abrading element and said proximal end of said drive rod being configured to engage to said drive mechanism.

9. The device of claim 1, wherein said drive mechanism is disposed at least in part in said handle.

10. The device of claim 1, wherein said power source is disposed at least in part in said handle.

11. The device of claim 1, including a drive rod disposed within said shaft, said drive rod being rotatably driven by said drive mechanism and including a gear at its distal end, said gear being configured to mate with corresponding teeth on said abrading element.

12. The device of claim 11, wherein said abrading element includes first and second abrading surfaces, each of said abrading surfaces including teeth formed thereon to engage with said gear of said drive rod, said gear and said teeth being configured such that said two abrading surfaces are rotated in opposite directions as said drive rod is rotated by the drive mechanism.

13. The device of claim 1, wherein said abrading element is driven in one of a reciprocating, arcuate, rotary, oscillatory, and vibratory motion by said drive mechanism.

14. The device of claim 1, wherein said abrading element includes at least two abrading surfaces for simultaneously creating predetermined surface contours on the respective end plates of the adjacent vertebral bodies.

15. The device of claim 1, wherein said abrading element includes a non-abrading surface formed on a side of said abrading element opposite said abrading surface, said non-abrading surface being configured to allow a surgeon to increase the pressure of said abrading surface against one of the adjacent vertebral bodies.

16. The device of claim 1, including at least one stop member to limit the depth of travel of said abrading element into the spine.

17. The device of claim 16, wherein said stop member is adjustable so as to select the allowed depth of penetration of said abrading element into the spine.

18. The device of claim 17, wherein said stop member is configured as a sleeve surrounding a part of said shaft, said sleeve being movable a predetermined amount on said handle portion to select the permissible depth of penetration of said abrading element into the spine.

19. The device of claim 18, including means for releasably adjusting the position of said stop member relative to said shaft.

20. The device of claim 19, wherein said releasably adjusting means includes a spring biased lever, said lever having an engaging portion at one end configured to mate with a plurality of notches configured in said shaft.

21. The device of claim 1, wherein said drive mechanism is operable to move said abrading element in at least two degrees of freedom.

22. The device of claim 1, wherein said abrading element has at least a top abrading surface and a bottom abrading surface.

23. The device of claim 22, wherein said abrading element includes a leading edge configured as a bone cutting surface.

24. The device of claim 22, wherein at least one of said top and bottom surfaces of said abrading element are convex.

25. The device of claim 22, wherein at least said top and bottom surfaces of said abrading element are tapered outwardly from a front surface of said abrading element.

26. The device of claim 1, including a rechargeable battery power source for powering said drive mechanism.

27. The device of claim 1, including a suction mechanism for removing bits of debris created by said abrading surface of the abrading element.

28. The device of claim 1, including an irrigation channel for delivering irrigation fluid to the surgical site.

29. An abrading element for preparing a space between adjacent vertebral bodies to receive an insert, said abrading element having at least one abrading surface and being mountable on a device capable of moving said abrading element to cause said abrading surface to create at least one surface having a predetermined contour in the end plate of at least one of said adjacent vertebral bodies, said abrading surface having a width selected to substantially match the overall width of the insert to be received between the adjacent vertebral bodies, said abrading surface being configured and oriented such that it is generally parallel to the surface formed in the end plate of said vertebral body when in use.

30. The abrading element of claim 29, wherein said abrading element has a top surface and bottom surface.

31. The abrading element of claim 30, wherein at least one of said top and bottom surfaces of said abrading element are roughened to provide said abrading surface.

32. The abrading element of claim 29, wherein said abrading element has a leading edge configured to cut into the vertebral body as the abrading element is inserted into the spine.

33. The abrading element of claim 30, wherein at least one of said top and bottom surfaces of said abrading element are convex.

34. The abrading element of claim 30, wherein at least one of said top and bottom surfaces of said abrading element are tapered outwardly from said front surface of said abrading element.

35. A device for preparing a space in a human spine across a disc space and into the end plates of adjacent vertebral bodies to receive an interbody spinal insert, comprising:
   a handle;
   a shaft operably connected to said handle;
   a mounting member disposed at a distal end of said shaft;
   a drive mechanism;
   a power source for powering said drive mechanism;
   an abrading element mountable on said mounting member; and
   a coupling mechanism for connecting and imparting motion from said drive mechanism to said abrading element, said abrading element having at least one broad abrading surface selected to remove bone from and create a predetermined surface contour in at least one of the end plates of the adjacent vertebral bodies as said abrading element is moved by the drive mechanism, said abrading surface being configured to substantially match in width and contour a surface of the interbody spinal insert and the predetermined surface contour.

36. The device of claim 35, wherein said drive mechanism moves said abrading element in a plane generally parallel to the predetermined surface contour to be formed in the vertebral body, and said movement of said abrading element is selected from the group consisting of rotary, oscillatory, vibratory, and reciprocatory.

37. A device for preparing a space to receive an interbody insert within and between the adjacent surfaces of vertebral bodies disposed adjacent a disc space, comprising:
   a handle, said handle containing at least a portion of a drive mechanism;
   a shaft operably connected to and extending from said handle;
   a mounting element positioned at a distal end of said shaft; and
   an abrading element disposed on said mounting element and operably connected to said drive mechanism to be driven thereby, said abrading element having a surface and said surface having a width substantially the same as the width of the insert to be implanted, said surface having a configuration adapted to remove bone from said vertebral bodies to prepare said vertebral bodies to receive said insert, said surface of said abrading element also being configured to be generally parallel to a receiving surface that is formed on said vertebral body by said device.

38. The device of claim 37, wherein said abrading element includes first and second outwardly facing opposed abrading surfaces.

39. The device of claim 37, wherein said device includes a stop mechanism for limiting the depth of insertion of the device into the disc space.

40. The device of claim 37, wherein said abrading surface has a width, said width substantially matches the width of the nucleus pulposus of a disc space in which it is inserted.

41. The device of claim 37, wherein said abrading surface is substantially planar.

42. The device of claim 37, wherein said abrading surface has a convex configuration.

43. The device of claim 37, wherein said abrading element includes outwardly facing first and second abrading surfaces, and said first and second abrading surfaces are inclined relative to one another.

44. The device of claim 38, wherein said two outwardly facing, opposed abrading surfaces are substantially parallel to one another.

45. The device of claim 37, wherein said drive mechanism is adapted to produce a rotary movement of said abrading element about an axis generally perpendicular to a longitudinal axis of said shaft and a general plane of the vertebral end plate.

46. The device of claim 37, wherein said drive mechanism is adapted to produce an oscillating rotation of the abrading element.

47. The device of claim 37, wherein said drive mechanism is adapted to produce an oscillating rotation of the abrading element, wherein said oscillating rotation is from 20° to 45° to either side of the longitudinal axis of said shaft.

48. The device of claim 37, wherein said drive mechanism is adapted to produce a vibratory motion of the abrading element.

49. The device of claim 37, wherein said drive mechanism is adapted to produce a reciprocating motion of the abrading element.

50. The device of claim 37, wherein said device mechanism is powered by an energy source.

51. The device of claim 50, wherein said energy source is electrical.

52. The device of claim 51, wherein said energy source is a battery.

53. The device of claim 50, wherein said energy source is disposed, at least in part, within said handle.

54. The device of claim 37, wherein said device mechanism comprises a gas driven turbine powered by a source of compressed gas.

55. The device of claim 37, wherein said mounting member has a surface opposite said surface of said abrading element for bearing against the vertebral body on the opposite side of the disc space.

56. The device of claim 55, wherein said bearing surface is arcuate.

57. The device of claim 55, wherein said bearing surface is smooth.

58. The device of claim 37, wherein said device is sterilizeable for use in surgery.

59. The device of claim 37, wherein said shaft is detachable from said handle.

60. The device of claim 37, wherein said mounting element is detachable from said shaft.

61. The device of claim 37, wherein said abrading element is detachable from said mounting element.

62. The device of claim 37, including a rotatable drive rod disposed within said shaft, said drive rod being operably connected to said drive mechanism and to said abrading element.

63. A method for preparing the disc space between adjacent vertebrae of a human spine to receive an insert therebetween, said method being performed with a device having a movable abrading element with an abrading surface that has a width substantially the same as the width of the insert to be implanted between said vertebrae, said method comprising the steps of:
    activating the device to cause the abrading surface to move;
    inserting the abrading surface into the space between the adjacent vertebrae;
    contacting the abrading surface of the abrading element against at least one of the adjacent vertebra to remove bone from the end plate of the vertebra that lies adjacent the disc space to form a surface on that vertebra, the surface of that vertebra having a contour that substantially matches the contour of a surface of the insert to be implanted and that substantially matches the contour of said abrading surface; and
    moving said abrading element relative to said device in a plane generally parallel to the surface contour to be formed in the vertebral body, the step of moving being selected from the group consisting of a reciprocating, arcuate, rotary, oscillatory, and vibratory motion.

64. The method of claim 63, wherein said abrading element includes first and second outwardly facing, opposed abrading surfaces, each having a width substantially the same as the width of the insert, and said contacting step includes the sub-step of simultaneously contacting and abrading the opposed surfaces of the vertebrae adjacent the disc space.

65. The method of claim 64, wherein the device is not activated until after the abrading surface has been inserted into the disc space.

66. The method of claim 63, wherein said device includes a stop mechanism for limiting the depth that the abrading element can be advanced into the disc space, and said contacting step includes the sub-step of linearly advancing the abrading element into the disc space until the stop mechanism contacts at least one of the adjacent vertebrae.

67. The method of claim 63, including the steps of measuring the width of the desired space to be formed between the adjacent vertebrae, and selecting an abrading element and corresponding abrading surface that matches the measured width.

68. The method of claim 64, including the further steps of removing the abrading surface from the disc space after completing the contacting step, and then positioning an insert into the space created between the adjacent vertebrae.

69. A device for preparing a space in the human spine to receive an insert between adjacent vertebral bodies, comprising:
    a handle;
    a shaft operably connected to said handle;
    a mounting member disposed at a distal end of said shaft;
    a drive mechanism;
    a power source operably connected to said drive mechanism;
    an abrading element mountable on said mounting member and movable by said drive mechanism, said abrading element having at least one abrading surface selected to create a predetermined surface contour in one of the adjacent vertebral bodies as the abrading element is moved by the drive mechanism; and
    a drive rod disposed within said shaft, said drive rod being rotatably driven by said drive mechanism being coupled to said abrading element.

70. The device of claim 69, wherein said abrading element includes first and second abrading surfaces, each of said abrading surfaces including teeth formed thereon to engage with said gear of said drive rod, said gear and said teeth being configured such that said two abrading surfaces are rotated in opposite directions as said drive rod is rotated by the drive mechanism.

71. The device of claim 69, wherein said mounting member is fixedly connected to said shaft.

72. The device of claim 69, wherein said mounting member is removably connected to said shaft.

73. The device of claim 69, wherein said mounting member includes an aperture and said abrading element includes a projection configured to fit within said aperture of said mounting member.

74. The device of claim 69, wherein said abrading surface is configured such that it is operated in a plane generally parallel to said surface contour formed in the vertebral body as the abrading element is moved by the drive mechanism.

75. The device of claim 69, wherein said mounting member includes a wall, an aperture, and a slot configured through said wall to communicate with said aperture.

76. The device of claim 69 including a mechanism that couples the abrading element to said drive mechanism.

77. The device of claim 76, wherein said coupling mechanism includes a drive rod having a proximal end and a distal end, said drive rod being adapted to be received in said shaft, said distal end of said drive rod being configured to couple to said abrading element to move said abrading element and said proximal end of said drive rod being configured to engage to said drive mechanism.

78. The device of claim 69, wherein said drive mechanism is disposed at least in part in said handle.

79. The device of claim 69, wherein said power source is disposed at least in part in said handle.

80. The device of claim 69, wherein said abrading element is driven in one of a reciprocating, arcuate, rotary, oscillatory, and vibratory motion by said drive mechanism.

81. The device of claim 69, wherein said abrading element includes at least two abrading surfaces for simultaneously creating predetermined surface contours on the respective end plates of the adjacent vertebral bodies.

82. The device of claim 69, wherein said abrading element includes a non-abrading surface formed on a side of said abrading element opposite said abrading surface, said non-abrading surface being configured to allow a surgeon to increase the pressure of said abrading surface against one of the adjacent vertebral bodies.

83. The device of claim 69, including at least one stop member to limit the depth of travel of said abrading element into the spine.

84. The device of claim 83, wherein said stop member is adjustable so as to select the allowed depth of penetration of said abrading element into the spine.

85. The device of claim 84, wherein said stop member is configured as a sleeve surrounding a part of said shaft, said sleeve being movable a predetermined amount on said handle portion to select the permissible depth of penetration of said abrading element into the spine.

86. The device of claim 85, including means for releasably adjusting the position of said stop member relative to said shaft.

87. The device of claim 86, wherein said releasably adjusting means includes a spring biased lever, said lever having an engaging portion at one end configured to mate with a plurality of notches configured in said shaft.

88. The device of claim 69, wherein said drive mechanism is operable to move said abrading element in at least two degrees of freedom.

89. The device of claim 69, wherein said abrading element has at least a top abrading surface and a bottom abrading surface.

90. The device of claim 89, wherein said abrading element includes a leading edge configured as a bone cutting surface.

91. The device of claim 89, wherein at least one of said top and bottom surfaces of said abrading element are convex.

92. The device of claim 89, wherein at least said top and bottom surfaces of said abrading element are tapered outwardly from a front surface of said abrading element.

93. The device of claim 69, including a rechargeable battery power source for powering said drive mechanism.

94. The device of claim 69, including a suction mechanism for removing bits of debris created by said abrading surface of the abrading element.

95. The device of claim 69, including an irrigation channel for delivering irrigation fluid to the surgical site.

96. A device for preparing a space in the human spine to receive an insert between adjacent vertebral bodies, comprising:
 a handle;
 a shaft operably connected to said handle;
 a mounting member disposed at a distal end of said shaft;
 a drive mechanism;
 a power source operably connected to said drive mechanism; and
 an abrading element mountable on said mounting member and movable by said drive mechanism, said abrading element having at least one abrading surface selected to create a predetermined surface contour in one of the adjacent vertebral bodies as the abrading element is moved by the drive mechanism, said abrading element having a non-abrading surface formed on a side of said abrading element opposite said abrading surface.

97. The device of claim 96, wherein said mounting member is fixedly connected to said shaft.

98. The device of claim 96, wherein said mounting member is removably connected to said shaft.

99. The device of claim 96, wherein said mounting member includes an aperture and said abrading element includes a projection configured to fit within said aperture of said mounting member.

100. The device of claim 96, wherein said abrading surface is configured such that it is operated in a plane generally parallel to said surface contour formed in the vertebral body as the abrading element is moved by the drive mechanism.

101. The device of claim 96, wherein said mounting member includes a wall, an aperture, and a slot configured through said wall to communicate with said aperture.

102. The device of claim 96 including a mechanism that couples the abrading element to said drive mechanism.

103. The device of claim 102, wherein said coupling mechanism includes a drive rod having a proximal end and a distal end, said drive rod being adapted to be received in said shaft, said distal end of said drive rod being configured to couple to said abrading element to move said abrading element and said proximal end of said drive rod being configured to engage to said drive mechanism.

104. The device of claim 96, wherein said drive mechanism is disposed at least in part in said handle.

105. The device of claim 96, wherein said power source is disposed at least in part in said handle.

106. The device of claim 96, including a drive rod disposed within said shaft, said drive rod being rotatably driven by said drive mechanism and including a gear at its distal end, said gear being configured to mate with corresponding teeth on said abrading element.

107. The device of claim 106, wherein said abrading element includes first and second abrading surfaces, each of said abrading surfaces including teeth formed thereon to engage with said gear of said drive rod, said gear and said teeth being configured such that said two abrading surfaces are rotated in opposite directions as said drive rod is rotated by the drive mechanism.

108. The device of claim 96, wherein said abrading element is driven in one of a reciprocating, arcuate, rotary, oscillatory, and vibratory motion by said drive mechanism.

109. The device of claim 96, wherein said abrading element includes at least two abrading surfaces for simultaneously creating predetermined surface contours on the respective end plates of the adjacent vertebral bodies.

110. The device of claim 96, including at least one stop member to limit the depth of travel of said abrading element into the spine.

111. The device of claim 110, wherein said stop member is adjustable so as to select the allowed depth of penetration of said abrading element into the spine.

112. The device of claim 111, wherein said stop member is configured as a sleeve surrounding a part of said shaft, said sleeve being movable a predetermined amount on said handle portion to select the permissible depth of penetration of said abrading element into the spine.

113. The device of claim 112, including means for releasably adjusting the position of said stop member relative to said shaft.

114. The device of claim 113, wherein said releasably adjusting means includes a spring biased lever, said lever having an engaging portion at one end configured to mate with a plurality of notches configured in said shaft.

115. The device of claim 96, wherein said drive mechanism is operable to move said abrading element in at least two degrees of freedom.

116. The device of claim 96, wherein said abrading element has at least a top abrading surface and a bottom abrading surface.

117. The device of claim 116, wherein said abrading element includes a leading edge configured as a bone cutting surface.

118. The device of claim 116, wherein at least one of said top and bottom surfaces of said abrading element are convex.

119. The device of claim 116, wherein at least said top and bottom surfaces of said abrading element are tapered outwardly from a front surface of said abrading element.

120. The device of claim 96, including a rechargeable battery power source for powering said drive mechanism.

121. The device of claim 96, including a suction mechanism for removing bits of debris created by said abrading surface of the abrading element.

122. The device of claim 96, including an irrigation channel for delivering irrigation fluid to the surgical site.

123. A device for preparing a space in the human spine to receive an insert between adjacent vertebral bodies, comprising:
    a handle;
    a shaft operably connected to said handle;
    a mounting member disposed at a distal end of said shaft;
    a drive mechanism;
    a power source operably connected to said drive mechanism; and
    an abrading element mountable on said mounting member and movable by said drive mechanism, said abrading element having at least one abrading surface selected to create a predetermined surface contour in one of the adjacent vertebral bodies as the abrading element is moved by the drive mechanism.

124. The device of claim 123, wherein said abrading element has at least a top abrading surface and a bottom abrading surface.

125. The device of claim 124, wherein said abrading element includes a leading edge configured as a bone cutting surface.

126. The device of claim 123, wherein said mounting member is fixedly connected to said shaft.

127. The device of claim 123, wherein said mounting member is removably connected to said shaft.

128. The device of claim 123, wherein said mounting member includes an aperture and said abrading element includes a projection configured to fit within said aperture of said mounting member.

129. The device of claim 123, wherein said abrading surface is configured such that it is operated in a plane generally parallel to said surface contour formed in the vertebral body as the abrading element is moved by the drive mechanism.

130. The device of claim 123, wherein said mounting member includes a wall, an aperture, and a slot configured through said wall to communicate with said aperture.

131. The device of claim 123 including a mechanism that couples the abrading element to said drive mechanism.

132. The device of claim 131, wherein said coupling mechanism includes a drive rod having a proximal end and a distal end, said drive rod being adapted to be received in said shaft, said distal end of said drive rod being configured to couple to said abrading element to move said abrading element and said proximal end of said drive rod being configured to engage to said drive mechanism.

133. The device of claim 123, wherein said drive mechanism is disposed at least in part in said handle.

134. The device of claim 123, wherein said power source is disposed at least in part in said handle.

135. The device of claim 123, including a drive rod disposed within said shaft, said drive rod being rotatably driven by said drive mechanism and including a gear at its distal end, said gear being configured to mate with corresponding teeth on said abrading element.

136. The device of claim 135, wherein said abrading element includes first and second abrading surfaces, each of said abrading surfaces including teeth formed thereon to engage with said gear of said drive rod, said gear and said teeth being configured such that said two abrading surfaces are rotated in opposite directions as said drive rod is rotated by the drive mechanism.

137. The device of claim 123, wherein said abrading element is driven in one of a reciprocating, arcuate, rotary, osciallatory, and vibratory motion by said drive mechanism.

138. The device of claim 123, wherein said abrading element includes at least two abrading surfaces for simultaneously creating predetermined surface contours on the respective end plates of the adjacent vertebral bodies.

139. The device of claim 123, wherein said abrading element includes a non-abrading surface formed on a side of said abrading element opposite said abrading surface, said non-abrading surface being configured to allow a surgeon to increase the pressure of said abrading surface against one of the adjacent vertebral bodies.

140. The device of claim 123, including at least one stop member to limit the depth of travel of said abrading element into the spine.

141. The device of claim 140, wherein said stop member is adjustable so as to select the allowed depth of penetration of said abrading element into the spine.

142. The device of claim 141, wherein said stop member is configured as a sleeve surrounding a part of said shaft, said sleeve being movable a predetermined amount on said handle portion to select the permissible depth of penetration of said abrading element into the spine.

143. The device of claim 142, including means for releasably adjusting the position of said stop member relative to said shaft.

144. The device of claim 143, wherein said releasably adjusting means includes a spring biased lever, said lever having an engaging portion at one end configured to mate with a plurality of notches configured in said shaft.

145. The device of claim 123, wherein said drive mechanism is operable to move said abrading element in at least two degrees of freedom.

146. The device of claim 123, wherein at least one of said top and bottom surfaces of said abrading element are convex.

147. The device of claim 123, wherein at least said top and bottom surfaces of said abrading element are tapered outwardly from a front surface of said abrading element.

148. The device of claim 123, including a rechargeable battery power source for powering said drive mechanism.

149. The device of claim 123, including a suction mechanism for removing bits of debris created by said abrading surface of the abrading element.

150. The device of claim 123, including an irrigation channel for delivering irrigation fluid to the surgical site.

151. An abrading element for preparing a space between adjacent vertebral bodies to receive an insert, said abrading element having at least one abrading surface and being mountable on a device capable of moving said abrading element to cause said abrading surface to create at least one surface having a predetermined contour in the end plate of at least one of said adjacent vertebral bodies, said abrading surface having a width selected to substantially match the overall width of the insert to be received between the adjacent vertebral bodies and a perimeter that is at least in part arcuate, said abrading element having a leading edge configured to cut into the vertebral body as the abrading element is inserted into the spine.

152. The abrading element of claim 151, wherein said abrading element has a top surface and bottom surface.

153. The abrading element of claim 152, wherein at least one of said top and bottom surfaces of said abrading element are roughened to provide said abrading surface.

154. The abrading element of claim 152, wherein at least one of said top and bottom surfaces of said abrading element are convex.

155. The abrading element of claim 152, wherein at least one of said top and bottom surfaces of said abrading element are tapered outwardly from said front surface of said abrading element.

156. The abrading element of claim 151, wherein said abrading surface is configured and oriented such that it is generally parallel to the surface formed in the end plate of said vertebral body when in use.

157. A device for preparing a space in a human spine across a disc space and into the end plates of adjacent vertebral bodies to receive an interbody spinal insert, comprising:

a handle;

a shaft operably connected to said handle;

a mounting member disposed at a distal end of said shaft;

a drive mechanism;

a power source for powering said drive mechanism;

an abrading element mountable on said mounting member; and a coupling mechanism for connecting and imparting motion from said drive mechanism to said abrading element, said abrading element having at least one broad abrading surface selected to remove bone from and create a predetermined surface contour in at least one of the end plates of the adjacent vertebral bodies as said abrading element is moved by the drive mechanism in a plane generally parallel to the predetermined surface contour to be formed in the vertebral body, said movement of said abrading element being selected from the group consisting of rotary, oscillatory, vibratory, and reciprocatory, said abrading surface being configured to substantially match in width and contour a surface of said interbody spinal insert.

158. An abrading element for preparing a space between adjacent vertebral bodies to receive an insert, said abrading element having a top abrading surface for abrading bone and a bottom surface opposite said top surface adapted to mount on a device capable of moving said abrading element to cause said abrading surface to create at least one surface having a predetermined contour in the end plate of at least one of said adjacent vertebral bodies, said abrading surface having a width selected to substantially match the overall width of the insert to be received between the adjacent vertebral bodies, said abrading element having a leading edge configured to cut into the vertebral body as the abrading element is inserted into the spine.

159. The abrading element of claim 158, wherein said top surface of said abrading element is roughened to provide said abrading surface.

160. The abrading element of claim 158, wherein said top surface of said abrading element is convex.

161. The abrading element of claim 158, wherein said top surface of said abrading element is tapered outwardly from a front surface of said abrading element.

162. The abrading element of claim 158, wherein said abrading surface is configured and oriented such that it is generally parallel to the surface formed in the end plate of said vertebral body when in use.

* * * * *

UNITED STATES PATENT AND TRADEMARK OFFICE

CERTIFICATE OF CORRECTION

PATENT NO: 6,083,228

DATED: July 4, 2000

INVENTOR: Gary K. Michelson

It is hereby certified that an error appears in the above-identified patent and that said Letters Patent is hereby corrected as shown below:

Column 13, claim 1, line 5: change "a" to --an outer--;

line 6: after "said" insert --outer--;

line 11: before "and" insert --on said distal end of said outer shaft--;

line 13: delete "predetermined".

Signed and Sealed this

Third Day of April, 2001

*Attest:*

NICHOLAS P. GODICI

*Attesting Officer*      Acting Director of the United States Patent and Trademark Office